Figure 1:
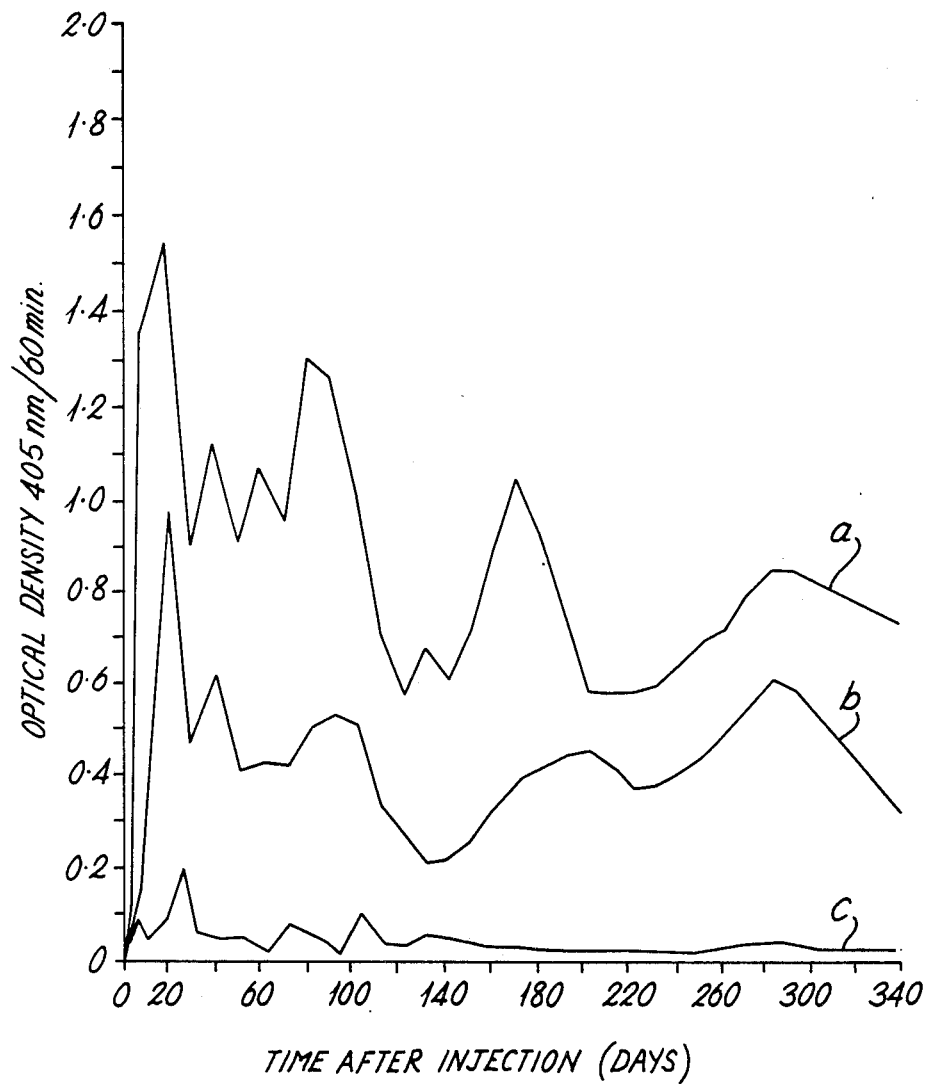

United States Patent [19]

New et al.

[11] Patent Number: 4,661,346

[45] Date of Patent: Apr. 28, 1987

[54] IMMUNOLOGICAL COMPOSITIONS INCLUDING A PEPTIDE AND OSMIUM OR RUTHENIUM TETROXIDE

[75] Inventors: Roger R. C. New, Liverpool; Robert D. G. Theakston, Formby, both of England

[73] Assignee: National Research Development Corporation, England

[21] Appl. No.: 719,274

[22] PCT Filed: Aug. 1, 1984

[86] PCT No.: PCT/GB84/00265

§ 371 Date: Mar. 28, 1985

§ 102(e) Date: Mar. 28, 1985

[87] PCT Pub. No.: WO85/00749

PCT Pub. Date: Feb. 28, 1985

[30] Foreign Application Priority Data

Aug. 4, 1983 [GB] United Kingdom ................. 8321009

[51] Int. Cl.⁴ ............................................ A61K 39/39
[52] U.S. Cl. ........................................ 424/85; 424/86; 424/88; 424/89; 514/6; 530/387; 530/399; 530/403; 530/806; 530/856
[58] Field of Search ........... 514/6; 260/112 B, 112 R; 424/85, 88, 86, 89; 530/387, 399, 403, 806, 856

[56] References Cited

U.S. PATENT DOCUMENTS

| 3,406,121 | 10/1968 | Jones | 252/408 |
|---|---|---|---|
| 3,743,720 | 7/1973 | Fosker et al. | 424/88 |
| 4,196,191 | 4/1980 | Almeida et al. | 424/89 |
| 4,405,720 | 9/1983 | Merril | 436/86 |
| 4,551,431 | 11/1985 | Pierce | 514/6 X |

FOREIGN PATENT DOCUMENTS

| 1942161 | 2/1970 | Fed. Rep. of Germany . |
|---|---|---|
| 1515226 | 6/1978 | United Kingdom . |
| 1592496 | 7/1981 | United Kingdom . |
| 1603597 | 11/1981 | United Kingdom . |

OTHER PUBLICATIONS

Chem. Abstracts, 49, 4738d-e, Bahr, 1955.
Chem. Abstracts, 63, 7237c, Hake, 1965.
Chem. Abstracts, 64, 16183e, Eddy et al., 1966.
Chem. Abstracts, 93, 2725j, Mitsui et al., 1980.
Chem. Abstracts, 94, 18725w, Deetz et al., 1981.
Chem. Abstracts, 98, 157265m, Johansson et al., 1983.
Chem. Abstracts, vol. 33, 1939, 78371-2, Aitoff et al.
Chem. Abstrats, vol. 37, 1943, 1776-7, Schultz et al.
Chem. Abstracts, vol. 69, 1968, 41216t, Belluscio.
Chem. Abstracts, vol. 71, 1969, 67856t, Hopwood.
Rote Liste, 1979, Editio Cantor, No. 08093D.
Henricson et al., Acta orthop. scand., 1982, 53, pp. 17 to 21.
Manicourt et al., Scand. J. Rheumatology, 1981, 10, pp. 43 to 48.
New Ways to use Metals for Arthritis, Science, 1981, 212.
Komorowsak et al., Biochimica et Biophysica Acta, 1982, 686, pp. 94 to 98.
The New England Journal of Medicine, Jul. 1984, 311, pp. 56 to 57.
Theakston et al., Proceedings of the International Society of Toxicology Meeting of Aug. 1983.
Johansson et al., J. Neuroscience Methods, 1983, 7, pp. 185-193.
Hopwood, Histochemie, 1969, 18, pp. 250 to 260.

*Primary Examiner*—Howard E. Schain
*Attorney, Agent, or Firm*—Jacobs & Jacobs

[57] ABSTRACT

Immunogenic compositions comprising a peptide or protein material together with an oxide selected from the group consisting of osmium tetroxide, potassium permanganate and ruthenium oxide, and antibodies raised by the use of such a composition, are of value in therapy and diagnosis, for example in the context of snake venom vaccines.

17 Claims, 5 Drawing Figures

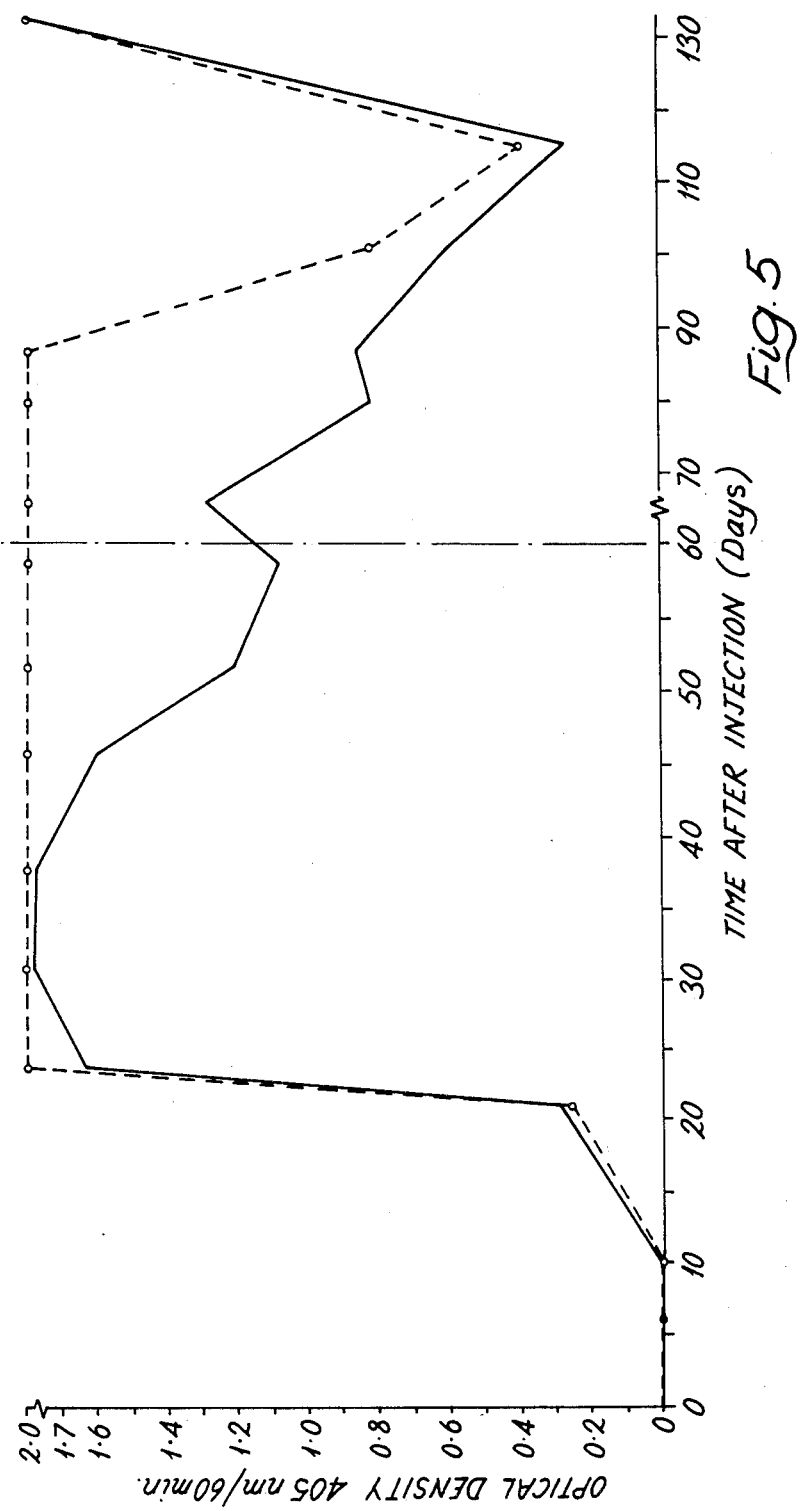

IMMUNOLOGICAL COMPOSITIONS INCLUDING A PEPTIDE AND OSMIUM OR RUTHENIUM TETROXIDE

This invention relates to immunological compositions and the use thereof.

Antigenic materials are widely used in both a human and a veterinary context in prophylactic therapy against, or in the treatment of, infectious diseases and of other types of undesirable biological reactions such as those induced through the bite of a snake or other venomous creature. The antigenic material may be used either in an active immunisation schedule through direct administration of the material to the intended recipient or in a passive inmunisation schedule where it is used to produce antibodies which are then administered to the recipient. It is often the case, however, that an antigenic material may not be as immunogenic as could be desired, thereby necessitating the use of a plurality of injections. As an alternative, or in addition to the use of repeated injections, an adjuvant may be used in order to increase the immune response provoked by the antigenic material. However, the effective adjuvants at present available, for example Freund's incomplete and complete adjuvants, have disadvantages, particularly for human use. For some time, therefore, attempts have been made to discover new forms of adjuvant which would simplify immunisation procedures and reduce the amounts of antigenic material required or amplify the response to a given quantity of antigenic material.

The quite unexpected finding has now been made that the members of a small group of oxides comprising osmium tetroxide, potassium permanganate and ruthenium tetroxide are able to enhance the immune response provoked by antigenic materials of certain types, both in terms of the level of the initial response and the duration of the response.

Osmium tetroxide, in particular, has previously been widely used as a fixing agent in electron microscopic studies of biological samples and in this context its reaction with the proteins lysozyme and ovalbumin has been studied. It has also received some use in the treatment of rheumatoid synovitis through direct administration into the knee. However, these uses are quite unrelated to the context of the present invention which involves the first use in therapy of an immunogenic composition (i.e. a composition producing an immunological reaction) comprising a peptide or protein material and osmium tetroxide, potassium permanganate or ruthenium tetroxide, specifically in the production of immunological reactions.

According to the present invention a composition for use in the production of an immunological reaction to a peptide or protein material comprises said peptide or protein material together with an oxide selected from the group consisting of osmium tetroxide, potassium permanganate and ruthenium tetroxide.

Without imposing any limitation upon the present invention with respect to the nature of such binding, which is however believed to be of a covalent nature, it may be stated that the peptide or protein material and the oxide are in general believed to be associated in some form of binding. Indeed, it is preferred, in order to produce a suitable form of composition lacking toxic side effects, to employ in the preparation of the composition a specific step, usually involving dialysis, which substantially removes low molecular weight products which are derived from the oxide, particularly the metal and the oxide itself, which are not either peptide- or protein-bound or lipid bound (when the composition is a microvesicle preparation as described hereinafter). The oxide of particular interest for use in the present invention is osmium tetroxide and for the sake of simplicity only therefore, the invention is further described by reference to that oxide, although it will be appreciated that potassium permanganate and ruthenium oxide may in general be used in an exactly analogous manner.

A wide variety of peptide and protein antigenic materials (the term "peptide or protein material" as used herein includes materials which consist of a compound comprising a peptide or protein portion as well as a portion having a different form of structure and also mixtures of a peptide or protein compound and a compound of different structure) may be used in compositions according to the present invention, more than one such material being included if desired. The invention is applicable to peptide and protein materials which are of use in vaccines for use in prophylactic therapy and in other contexts, for example in immunological and serological reagents for the treatment of an existing disease, etc, and for the diagnostic use. Indeed, the invention is applicable to any peptide or protein material which will produce an immunological reaction (i.e. which will elicit a specific immune response), whether alone or in combination with a carrier, when formulated in combination with osmium tetroxide.

In the context of prophylactic vaccines for human adminstration, a variety of pathogenic antigens, and active fragments thereof, may be used as the antigenic material present in the vaccine. Examples include bacterial antigens and active components of such antigens including attenuated materials, materials worthy of specific mention being antigenic products of the cholera bacterium and toxoids such as diphtheria and tetanus toxoid (although it is possible that the effect of the osmium tetroxide in reducing toxicity as discussed hereinafter may even allow the use of toxins in some instances), as well as antigens useful in the treatment of conditions such as caries. Other examples of microbial antigens are viral antigens such as those derived from the influenza and rabies viruses, and active components thereof. The invention is also of interest, however, in relation to vaccines against other forms of pathogen such as protozoa, for example in the treatment of trypanosomiasis, parasitic worms, for example helminths, and fungi. The invention may also be used in the field of both human and animal contraception, for example in vaccination against gonadotrophin releasing hormone (Gn-RH or LHRH) when a hormone peptide is used as the antigenic material having value as a means of immunocastration in animals, as well as in the immunotherapy of cancer when a tumour specific antigen may be used as the antigenic material. One area of very particular interest is that in which the peptide or protein material is the toxic agent of various venomous creatures, particularly a toxic component (toxin) of the venom of snakes, whether in the form of the whole venom or an active component thereof. Snakes of particular interest in this context include species of the genus Echis, for example the carpet viper, *E. carinatus*, species of the genus Naja, for example *N. nigricollis*, species of the genus Bungarus, for example *B. candidus*, species of the genus Vipera, for example *V. russelli*, species of the genus Bitis, for example *B. arietans*, species of the genus Crotalus, for example *C. atrox*, species of the genus Bothrops, for example *B. atrox,* pit vipers of the species of the genus Trimeresurus, for example *T. albolabris, T. flavoviridis* and *T. macrops,* and also *Agkistrodon rhodostoma, Lachesis muta, Notechis scutatus, Oxyuranus scutellatus* and various others, for example the sea snake, *Laticuda semifasciata,* where erabutoxin of a molecular weight 6,800 purified from the venom is of value as the toxic agent.

The invention is also of considerable interest, and of similar wide applicability as regards the types of antigenic material discussed above, in the context of veterinary vaccines for both mammalian and avian administration, for example in the treatment of the viral foot and mouth disease in cattle and pigs.

It will be appreciated that a composition according to the present invention for the production of an immunological reaction against a specific peptide or protein, for example one such as is described above, may take one or more of several alternative forms depending on the individual circumstances. Thus, the composition may contain a peptide or protein material which comprises either the peptide or protein itself or an active fragment thereof since an immunological reaction directed against such a fragment will equally be directed against the whole compound, and this peptide or protein or fragment thereof which the material comprises may be present combined with a carrier in order to enhance the immunological reaction. Examples of carriers which may be used with smaller molecular weight materials are bovine serum albumin and turkey albumin, such being of particular use when raising antibodies in non-human hosts to snake venom toxins of smaller molecular weight, especially neurotoxins such as the *Naja kaonthia* toxin which has a molecular weight of only 7,700.

The development of immunity prophylactically may, however, be effected not only by the administration of a prophylactic vaccine which contains an antigenic material but also through passive immunisation with antibodies raised against that material. The use of a peptide or protein material/metal oxide composition provides a particularly convenient approach to the production of antibodies for passive immunization in a veterinary or particularly a human use and therefore comprises an important further aspect of the present invention. In this case, the particular peptide or protein material is adminstered to a suitable non-human host, usually an avian or mammalian host such as a sheep, and an antibody preparation obtained from the host through conventional techniques described in the art which usually involve the production of a purified antiserum. Alternative approaches include the use of the invention to stimulate the immunological reaction to a peptide or protein material which is used to produce immunocytes sensitized thereto for use in the production of a hybridoma. The present invention thus includes a method for use in the production of antibodies to a peptide or protein material which comprises administering said peptide or protein material together with an oxide selected from the group consists of osmium tetroxide, potassium permanganate and ruthenium tetroxide to a non-human host and thereafter isolating from the host either cells sensitised to, or antibodies to, said peptide or protein material. The peptide or protein materials used in such a method may include all of those discussed hereinbefore in relation to prophylactic vaccines. However, one example of the use of such a method which is of some particular importance is with peptide or protein materials which are toxins, or the active components thereof, derived from venomous creatures such as snakes.

Such an antibody production method is, however, not only of interest in relation to the production of materials for use in the prophylatic immunisation. Thus, a group of diagnostic reagents of particular interest contains antibodies against various peptide or protein materials and such antibodies are conveniently produced using such a method. Examples of such diagnostic reagents are these containing antibody raised against an enzyme or enzymes, for example against horse-radish peroxidase, lactate dehydrogenase, glucose phosphokinase, glucose 6-phosphate dehydrogenase, alkaline and acid phosphatases, and also various other products containing antibody of human, mammalian and avian origin. Such reagents may contain mixtures of antibody and/or antibody fragments, and the antibody may be of various sub classes.

It should be stressed, however, that the present invention is of interest not only in relation to the development of immunity prophylactically but also in the context of pharmaceutical compositions for therapeutic use in the treatment of existing conditions. Such use may involve passive immunisation with antibodies produced in a suitable host as discussed above but there are also particular instances where direct administration to a human patient may be of especial value because of the rapidity of onset of the long lasting protective primary immune response generated by the compositions of the present invention. For example, in cases where a clinical disorder arises from the effect of a toxic or other material produced by an animal (in the broad sense of this word), parasite or micro-organism there may be an advantage in administering directly to the patient a composition containing the material together with osmium tetroxide rather than antibodies to the material raised in a host. Moreover, with disadvantageous biological reactions of slow onset, such as that produced by tetanus toxin, this direct approach may be of very particular value.

As will be seen from the foregoing discussion, the present invention thus includes not only a composition for use in the production of an immunological reaction to a peptide or protein material comprising such material together with an oxide selected from the group consisting of osmium tetroxide, potassium permanganate and ruthenium tetroxide, but also a composition for use in passive immunisation against such material (or alternatively for use as a diagnostic reagent) comprising antibodies thereto, which antibodies have been raised by administration to a non-human host of the material together with such an oxide. It will be appreciated that certain types of peptide and protein material as described above are of especial interest for incorporation in a composition whether for direct administration to a patient or in the production of antibodies for use in a passive immunisation procedure. In particular, and especially in the case of a composition containing osmium tetroxide as compared with potassium permanganate or ruthenium tetroxide, the present invention includes a composition in which the peptide or protein component thereof is other than ovalbumin or lysozyme, particularly being a microbial antigen (including viral and protozoal as well as bacterial antigens) or other non-human antigen, i.e. a material which normally exerts a toxic effect in man, for example a snake venom toxin.

Compositions of both types according to the present invention may take various forms but it is often the case, and this is also the case with compositions for use as diagnostic reagents, that the composition comprises either the peptide or protein material and osmium tetroxide, or antibodies to the material, and a physiologically acceptable diluent or carrier. Although a solid carrier may be used, for example a conventional carrier material such as starch, dextrin or magnesium stearate, it is more usually preferred to use a liquid diluent and where parenteral administration is proposed for a pharmaceutical composition, as will often be the case, then the composition may often conveniently be sterile and pyrogen free. Liquid compositions may be of an aqueous, oily or emulsified nature, for example being based on sterile, pyrogen-free isotonic saline. Compositions of particular interest for use in active immunisation, either of a patient or for the production of antibodies in a host for subsequent administration to a patient, are those in which at least a part of the peptide or protein material and of the osmium tetroxide is incorporated with liposomes or like materials (microvesicles). Microvesicles are widely described in the literature, being vesicular structures composed of lipid bilayers enclosing an aqueous compartment. Unilamellar bodies comprising a single lipid bilayer enclosing an aqueous compartment and oligolamellar and multilamellar bodies comprising a plurality of concentric lipid bilayers, often separated by an aqueous layer, enclosing a central aqueous compartment are all included by the term microvesicles. Compositions according to the present invention may comprise any of the various forms of microvesicles, ranging from smaller unilamellar microvesicles (SUVs) through larger unilamellar and oligolamellar vesicles produced by the reverse-phase evaporation technique (REVs) to the more conventional multilamellar liposomes (MLVs) containing varying numbers of layers. Such compositions will most usually contain the microvesicles in an aqueous medium which, if desired may contain further amounts of the same peptide or protein material in association with osmium tetroxide in addition to the amounts incorporated with the microvesicles. The compositions may be formulated in unit dosage form, i.e. in discrete portions containing a single dose or a multiple or fraction thereof.

It will be appreciated therefore that certain types of composition as described above are preferred, especially for certain materials, for example snake venoms and the like, and that in particular, the present invention includes a composition which comprises a peptide or a protein material and an oxide selected from the group consists of osmium tetroxide, potassium permanganate and ruthenium tetroxide incorporated with microvesicles. It should be noted, however, that with certain materials, for example horse-radish peroxidase, although the use of osmicated microvesicles enhances immunogenicty the use simply of an osmicated aqueous medium containing the material may give even greater enhancement.

The microvesicles for use in compositions according to the present invention may be formed by established procedures which are described in the art and comprise the admixture of a lipid in suitable form, for example as a thin film, with an aqueous medium and, where appropriate, may involve sonication. Variations described in the art for the preparation of particular forms of microvesicle may be applied in the present invention, particularly the technique of reverse phase evaporation, as described by Szoka and Papahadjopoulos in the Proceeedings of the National Academy of Sciences of the USA 1978, 75, 4194, which can lead to higher levels of entrapment of the peptide or protein.

Various forms of lipid may be used in preparing the microvesicles including both phospholipids and others but, among those described in the art, sphingomyelin is of particular interest since microvesicles prepared from this compound give strong enhancement of the immune response to an incorporated antigenic material. Sphingomyelin is also a phospholipid which is resistant to gut phospholipases and also to the phospholipases that may be present as the component of the snake venoms, which venoms represent a source of antigenic materials which are of particular interest in the context of the present invention. Moreover, membranes derived from sphingomyelin shows some level of resistance to degradation by bile salts, a property of interest in relation to the oral administration of microvesicle compositions. It will, however, often also be desirable to include cholesterol as a proportion of the total lipid content as a stabilising agent. Both sphingomyelin and cholesterol possess only one double bond so that osmium tetroxide should link these lipids inter-molecularly, rather than intra-molecularly, to give dimers.

Microvesicles according to the present invention may additionally contain other components, for example a material which provides a negative surface charge and in particular various negatively charged acidic compounds containing lipophilic chains including dicetyl phosphate, phosphatidyl serine, phosphatidyl glycerol, the more complex substance beef brain ganglioside, and especially phosphatidic acid. It is also possible to impart a positive surface charge to the microvesicles, for example by the use of stearylamine, although the use of negatively charged and particularly of neutral microvesicles is of greater interest in a pharmaceutical context.

A further type of additional component which may be mentioned specifically is one of the polymers described in the specification of UK Pat. No. GB 2026340 which confer additional in vivo stability on the microvesicles on storage. Other methods described in the art for increasing storage life may of course also be employed, for example freezing or freeze drying although there is some evidence that freeze drying may cause the antibody levels produced on administration of the microvesicles to be less sustained than would otherwise be the case.

Methods for adapting the procedures for the preparation of microvesicles to effect the incorporation of antigenic materials therewith are fully described in the art. Several approaches may be adopted to the incorporation of the osmium tetroxide. One approach is to prepare microvesicles incorporating the peptide or protein material, but lacking any osmium tetroxide, and then to treat the formed microvesicles with osmium tetroxide, for example by the addition of an aqueous solution of osmium tetroxide to an aqueous suspension of the microvesicles. A second approach is to add the osmium tetroxide to the peptide or protein material which is mixed with the lipid, or more usually with the aqueous component of the microvesicles, prior to the microvesicle formation. In particular, the initial stages of the preparation of multilamellar liposomes by the traditional technique and of unilamellar and oligolamellar microvesicles by the reverse phase evaporation technique usually involve the addition of an aqueous medium containing the peptide or protein material to the lipid, which is present as a film in the former case and in organic solution in the latter, and an appropriate amount of osmium tetroxide may be included in this aqueous solution.

Incorporation of osmium tetroxide in the aqueous medium used in the reverse phase evaporation technique also enables one to increase the level of entrapment of the peptide or protein material in the microvesicles in addition to the immunogenic effect of the osmium tetroxide. Thus, this technique involves the production of droplets of an aqueous medium containing the material to be encapsulated surrounded by a lipid monolayer. Subsequently, the dispersion of such droplets is dried down to give a gel which is then agitated, for example on a vortex mixer, to produce microvesicles incorporating the material in a large central aqueous compartment thereof. However, the production of such microvesicles incorporating a lipid bilayer necessarily involves some breakdown of the original droplets with a reduction in the eventual percentage level of incorporation of the material in the microvesicles. By stabilising the droplets containing the material, and by then drying these down in the presence of droplets of water surrounded by lipid, it is possible to ensure that the breakdown of droplets containing the material is limited, a major part of the breakdown and consequent provision of lipid deriving from these additional water-/lipid droplets not containing the material. Although osmium tetroxide itself is particularly suited to such a stabilising role, the inclusion of other materials may be considered for this purpose, for example the polymers of UK Pat. No. GB 2026340 referred to hereinbefore, or indeed with certain antigenic materials the level of stabilisation resulting from presence of the material may itself be sufficient. Such a procedure is of some general interest and the present invention thus includes a process for use in microvesicle production, for example in the method of Papahadjopoulos described in the specification of UK Patent Application No. GB 2015464, which comprises the removal of organic solvent from a dispersion of water/lipid droplets incorporating a material, for example a biologically active material such as a peptide or protein material as described herein, in the presence of water/lipid droplets substantially free from incorporated material, to thereby effect the preferential breakdown of such latter droplets, such a process conveniently employing an oxide selected from the group consisting of osmium tetroxide, potassium permanganate and ruthenium tetroxide, potassium permanganate and ruthenium tetroxide to enhance the stability of the droplets containing the material.

It is also possible to combine both approaches to the production of osmicated microvesicles by incorporating a first amount of osmium tetroxide prior to microvesicle formation and a second amount after formation. However, although the use of the reverse phase evaporation technique in conjunction with the incorporation of two separate amounts of osmium tetroxide gives good levels of entrapment of the peptide or protein material, it would appear that the immune response achieved is higher in the case of a single osmication treatment at a post-microvesicle formation stage. It is preferred, therefore, to use such singly osmicated microvesicles although it may be advantageous to use these microvesicles in the form of a composition which additionally comprises an aqueous medium, usually a solution, containing the peptide or protein material in association with osmium tetroxide. It will be appreciated that such a composition of singly, post-microvesicle formation, osmicated microvesicles containing the material and an osmicated aqueous solution of the material will usually be provided by the normal procedure of preparing the microvesicles and treating them with osmium tetroxide, unless steps are then taken to remove the osmium tetroxide which is peptide- or protein-bound but not microvesicle incorporated. Moreover whilst the use of microvesicles produced by the reverse phase evaporation technique has proved very successful, it is possible as explained hereinbefore to use any form of microvesicle preparation in the context of the present invention, the effect of the osmium tetroxide in enhancing immunogenicity often being sufficient to enable one to dispense with the need to use the more complex reverse phase evaporation technique in order to achieve higher levels of entrapment of the peptide or protein.

It is believed that the incorporation of the oxide with microvesicles can produce a stabilizing effect due to cross linking of the lipids and thus lead to an advantage in the case of microvesicle compositions which is additional to the immunogenic effect of the compound. For this reason, the present invention includes microvesicles which incorporate an active substance and an oxide selected from the group consisting of osmium tetroxide, potassium permanganate and ruthenium tetroxide. Such a substance may be a peptide or protein material as described above but may also be another form of antigenic material or indeed a substance having a biological activity which is not antigenic in nature, or indeed has a non-biological activity.

Compositions according to the present invention may be applied in a human or veterinary use either for the treatment of an existing condition or for prophylactic purposes, some form of parental administration such as injection, for example intravenous or subcutaneous, often being used, although oral administration is of interest, particularly with regard to prophylatic vaccines as opposed to compositions for passive immunisation. The present invention thus includes a method for the production of antibodies to a peptide or protein material in a patient which comprises administering to that patient either the said peptide or protein material together with osmium tetroxide or antibodies raised in another host by the administration to that host of said material, or a material containing it, together with osmium tetroxide. Booster treatments may be desirable in some cases, for example after an interval of 3 to 6 weeks and possibly again after a further period. Such a use is of particular interest in respect of peptides or protein material which comprise microbial antigens or venom toxins, or active components thereof.

The amounts of antigenic material or antibody incorporated in compositions according to the present invention may be similar to those used in existing vaccines incorporating such material or antibody, but it may often be possible with compositions for active immunisation to reduce these amounts in view of the increased iamunogenicity. Similarly, although additional adjuvants may be incorporated into compositions for active i ®munisation, this may likewise be unnecessary. By way of further guidance, it may be stated that with snake venom toxins a dose of 0.1 to 100 mg/kg, particularly 2.5 to 10 mg/kg, of the protein or peptide (excluding any carrier), or of antibody thereto in an amount which produces a similar titre on administration to such an amount of antigen, is generally suitable, and the doses for other proteins and peptides may be based on these ranges with appropriate adjustment (usually within the broadest range quoted) for difference of immunogenicity as compared with the snake venom toxin. The proportion of osmium tetroxide to the peptide or protein antigenic material may be varied according to the particular circumstances. However, as a guide, it may be stated that a proportion-by weight of osmium tetroxide:peptide or protein material in the range of 1:100 to 1:1, particularly of 1:10 to 1:5, is often suitable.

As mentioned previously, the use of osmium tetroxide leads to a prolonged effect so that, for example, one experimental group of mice was observed to exhibit high levels of snake venom antibody one year after receiving a single intravenous injection of the venom in microvesicle form, by which time some of the animals were dying of old age. The surviving mice were challenged with a subcutaneous, normally lethal, dose of a crude venom when sixty percent survived despite the lack of any booster injection since the single injection one year previously. Good results have also been obtained in rabbits and sheep as well as with mice. Moreover, it has been found that significant antibody titres in serum may be produced by the oral administration of snake venom in osmicated microvesicles. This is a very unusual result and is important since oral administration of vaccines, even if multiple doses are required, is a particularly convenient method of administration.

It should be stressed that, although the oxides and, in particular, osmium tetroxide are known to exhibit toxic effects under certain circumstances, microvesicles incorporating the oxide which have been dialysed to effect removal of any free osmium or osmium tetroxide have been widely used in experiments in mice, rabbits and sheep and have not shown any observable toxic effects attributable to osmium. Indeed, a very important additional advantage of the present invention, which is not seen with other adjuvants, is that the use of the oxide may reduce the level of any toxic effect arising from administration of the peptide or protein. Thus, it may thereby be possible to administer a dose of a venom higher than that which is normally lethal.

The invention is illustrated by the following Examples.

EXAMPLES

EXAMPLE 1

Preparation of microvesicles incorporating *Echis carinatus* venom and osmium tetroxide with single osmication step Sphingomyelin (20 mg) and cholesterol (8 mg)[1] are dissolved in chloroform (3 ml) contained in a broad round-bottomed glass tube. Ether (3 ml) is added and mixed with the chloroform solution, and to the mixture is then added phosphate buffered saline (1 ml) containing *E. carinatus* venom[2](10 mg), this aqueous solution being squirted into the organic solvent solution using a fine gauge needle. The glass tube is stoppered, shaken vigorously by hand for 5 seconds, and then placed in a 500 watt bath-type sonicator warmed to 30° C. After intermittent shaking for approximately 5 minutes an even dispersion is formed which does not separate into layers or have any water droplets floating on the surface. (the dispersion consists of a water-in-oil emulsion in which each droplet consists of an aqueous core coated with a monolayer of lipids aligned so that each phospholipid molecule has its polar group towards the aqueous centre of the droplet.) The dispersion is dried down slowly in the glass tube using a rotary evaporator to give a gel of close packed water droplets. Upon shaking this gel on a vortex mixer, some of the droplets collapse and lipid coats wrap round the other intact droplets giving large unilamellar microvesicles of high internal aqueous volume with a single bimolecular membrane shell.

[1] In a variation of this procedure the lipid is varied by using spingomyelin (12.7 mg) along, phosphatidyl choline (10.8 mg) and cholesterol (4 mg) or spingomyelin (10 mg) and cholesterol (4 mg).
[2] Unless otherwise indicated "venom" is used in these Examples to indicate whole venom rather than a fraction thereof.

The microvesicle preparation is centrifuged at 3,000 g and free protein separated in the supernatant. The pelleted microvesicles are suspended in phosphate buffered saline to provide 2 ml of a suspension which is treated with 0.1 ml of 1% w/v aqueous osmium tetroxide and allowed to stand at room temperature for 1 hour. The microvesicles are then dialysed extensively overnight at room temperature against water in order to remove any free osmium not incorporated with the microvesicles. The existence of cross linking of the membrane lipids by the osmium tetroxide is identifiable by the change of colour of the microvesicles from white to brown.

EXAMPLE 2

Preparation of microvesicles incorporating horseradish peroxidase and osmium tetroxide with single osmication step The procedure described in Example 1 is employed but with the *E. carinatus* venom (10 mg) being replaced by horseradish peroxidase (10 mg).

EXAMPLE 3

Preparation of microvesicles incorporating *Echis carinatus* venom and osmium tetroxide with double osmication step The procedure described in Example 1 is employed with a first modification that the phosphate buffered saline (1 ml) containing *E. carinatus* venom[1](10 mg) is treated with a solution of 0.1 ml of 1% w/v aqueous osmium tetroxide before being mixed with the original solution in chloroform/ether (6 ml) of sphingomyelin (20 mg) and cholesterol (8 mg). A second modification of the procedure of Example 1 involves mixing the droplets with a similar volume of an emulsion of droplets containing pure water, rather than venom solution and osmium tetroxide, prior to drying down to a gel and then vortexing. The remaining part of the procedure is as described in Example 1.[2]

[1] In a variation of the procedure described in Example 3, the *E. carinatus* venom is replaced by an antignic product of the cholera bacterium.
[2] In a further variation of the procedure of Example 3, the treatment with osmium tetroxide described in Example 1 is omitted to provide microvesicles which have been subjected to a single osication step, but one which is pre-microvesicle formation, rather than post-microvesicle formation as is the case with the single osmication step of Example 1. In a variation of either the double or the single osmication procedure the lipid is varied as described in the first footnote to Example 1.

EXAMPLE 4

Preparation of microvesicles incorporating various snake venoms and osmium tetroxide with double osmication step The procedure described in Example 3 is employed but replacing the 10 mg of *E. carinatus* venom by 10 mg of one of the following snake venoms: *Bungarus candidus, Laticauda semifascia:a. Naja kaouthia*,[3] *Naja Naja phillipinensis, Trimeresurus albolabris* and *Trimeresurus macrops.*

[3] The major neurotoxin of *N. kaouthia* venom has a molecular weight of only 7,700 and, in order to enhance antigenicity, preparations are therefore additionally made in which this neurotoxin is conjugated to Turkey ovalbumin and also to bovine serum albumin using 1 part of venom: 2 parts of alubumin by weight ad linking with glutaraldehyde in a conventional procedure. EXAMPLE 5

Preparation of microvesicles incorporationg a gonodotrophinreleasing hormone/bovine serum alubumin conjugate and osmium tetroxide with single or double osmication The procedure described in Example 1 or in Example 3 is employed but replacing the 10 mg of *E. carinatus* venom by 5 or 10 mg of a gonadotrophin releasing hormone (Gn-Rh)/bovine serum albumin (BSA) conjugate prepared as follows. Gn-Rh 0.1 mg; (synthetic, Hoechst) and BSA (0.1 mg; Cohn Fraction V, M.W. 70,000, Sigma Chemicals) are dissolved separately in distilled water (0.3 ml) to which is added 1-ethyl-3-(3-dimethylaminopropyl) carbodiimide hydrochloride (3.0 mg; Sigma Chemicals) dissolved in distilled water (0.3 ml). The mixture is allowed to stand overnight at room temperature to provide an aqueous solution of the desired conjugate.

EXAMPLE 6

Preparation of microvesicles incorporating *Echis carinatus* venom and potassium permanganate with double permanganation step The procedure described in Example 3 is employed but replacing the osmium tetroxide used on both occasions by the same weight of potassium permanganate.

EXAMPLE 7

Enhancement of activity in mice of intraveneously administered *Echis carinatus* venom through treatment with osmium tetroxide Mice are treated with different preparations of *E. carinatus* venom at varying dosages of the venom, groups of five mice being injected intravenously with an aliquot of each preparation, at the particular dosage rate, on a single occasion at day 0. The antibody levels resulting from the use of each form of preparation are assayed over an extended period of time using an ELISA assay based upon that described by Theakston et al, Lancet, 1977, (ii), 639. Fifty microlitres of whole heparinised blood is taken from the tail of each mouse and diluted in phosphate buffered saline (2.45 ml). Samples are stored at $-20°$ C. until measurement is carried out, when 0.3 ml of each sample is incubated at room temperature for 2 hours in wells of a plastic Nunc microliter plate pre-coated with crude unpurified *E. cari-carinatus* venom. After extensive washing, the amount of specific antibody remaining bound to venom protein on the walls of the well is assayed by incubation with alkaline phosphatase conjugated sheep-anti-mouse immunoglobulin, followed by washing, and measurmenet of the enzyme activity (over a time period of fifteen minutes to one hour) by observing the conversion of p-nitro phenyl phosphate to p-nitro phenol (the latter being measured spectrophotometrically in a Flow Multiskan multichannel photometer).

(A) The relative efficiency at generating antibodies was studied for three preparations consisting of: (a) 20 $\mu$g dose of venom in singly osmicated microvesicles prepared as described in Example 1; (b) 20 $\mu$g dose of venom in microvesicles prepared as described in Example 1 but omitting the osmium tetroxide; (c) 20 $\mu$g dose of venom as a simple 1% w/v solution in phosphate buffered saline.

The resulting antibody levels in terms of the optical density reading in the ELISA assay measured over a period of 340 days are shown in FIG. 1 where it will be seen that the non-osmicated microvesicle preparation (b) gives higher antibody levels than the aqueous solution preparation (c), but that the levels for the osmicated microvesicle preparation (a) are significantly higher than those for (b).

(B) The decrease in toxicity consequent upon the use of osmium tetroxide was found to allow the dose of venom administered in the form of singly osmicated microvesicles prepared as described in Example 1 to be increased from 20 ug to 50 $\mu$g, 100 pg and 200 $\mu$g. Even the highest of these increased doses was well tolerated by the mice and the comparative antibody levels in terms of the otpical density reading in the ELISA assay for the 20 $\mu$g, 50 $\mu$g and 100 $\mu$g doses are shown in FIG. 2 as plots (a), (b) and (c), respectively, the levels for the 200 $\mu$g dose lying consistently at the highest measurable value of 2.0.

Figure 2:
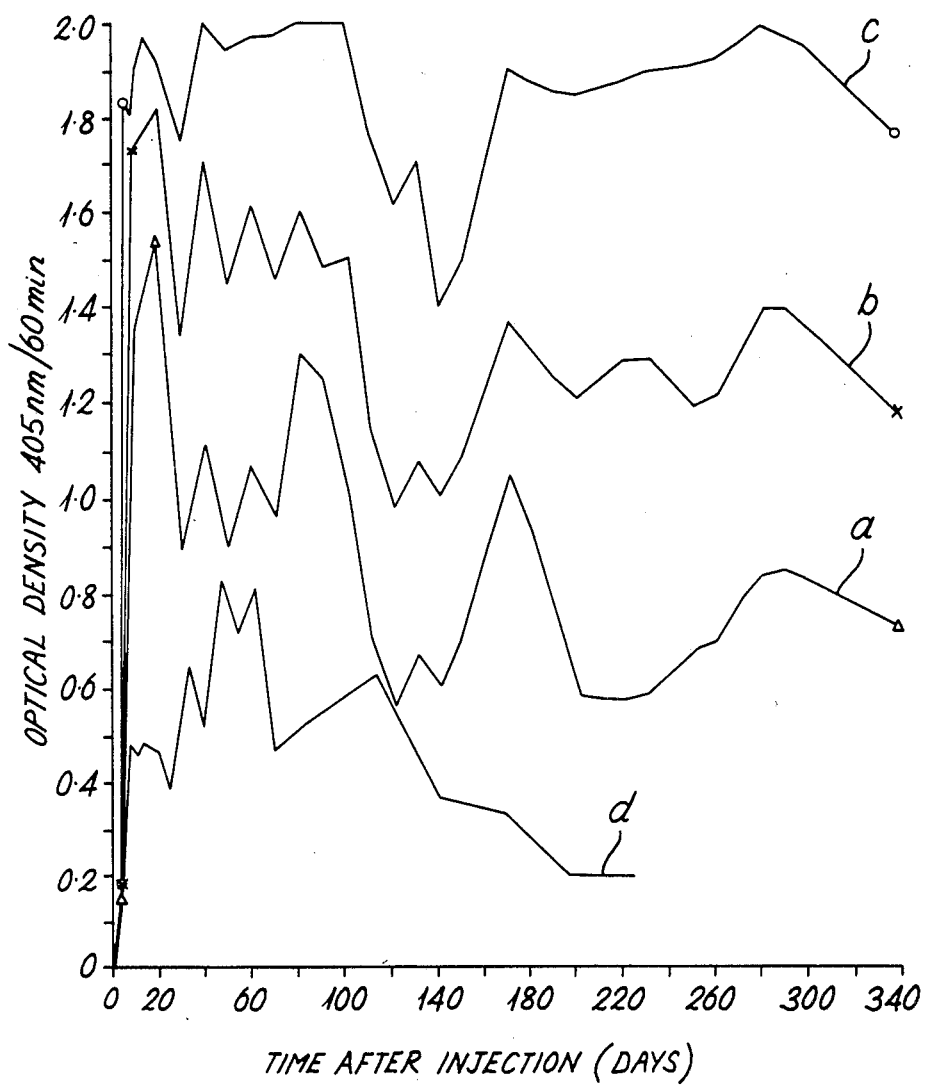

By way of comparison, the levels for a 100 $\mu$g dose of venom in doubly osmicated microvesicles prepared as described in Example 2 are additionally shown in FIG. 2 as plot (d). It will be seen that the immunogenic effect of the doubly osmicated microvesicles is significantly less, a dose of 100 $\mu$g producing lower levels than a dose of 20 $\mu$g of venom in the form of singly osmicated microvesicles.

(C) The relative efficiency at generating antibodies was studied for three preparations consisting of: (a) 150 $\mu$g dose of venom as a 1% w/v solution in phosphate buffered saline to which has been added 10% v/v of 1% w/v aqueous osmium tetroxide; (b) 720 $\mu$g dose of venom as a similar osmicated solution to that of (a); (c) 200 $\mu$g dose of venom in singly osmicated microvesicles prepared as described in Example 1.

Figure 3:
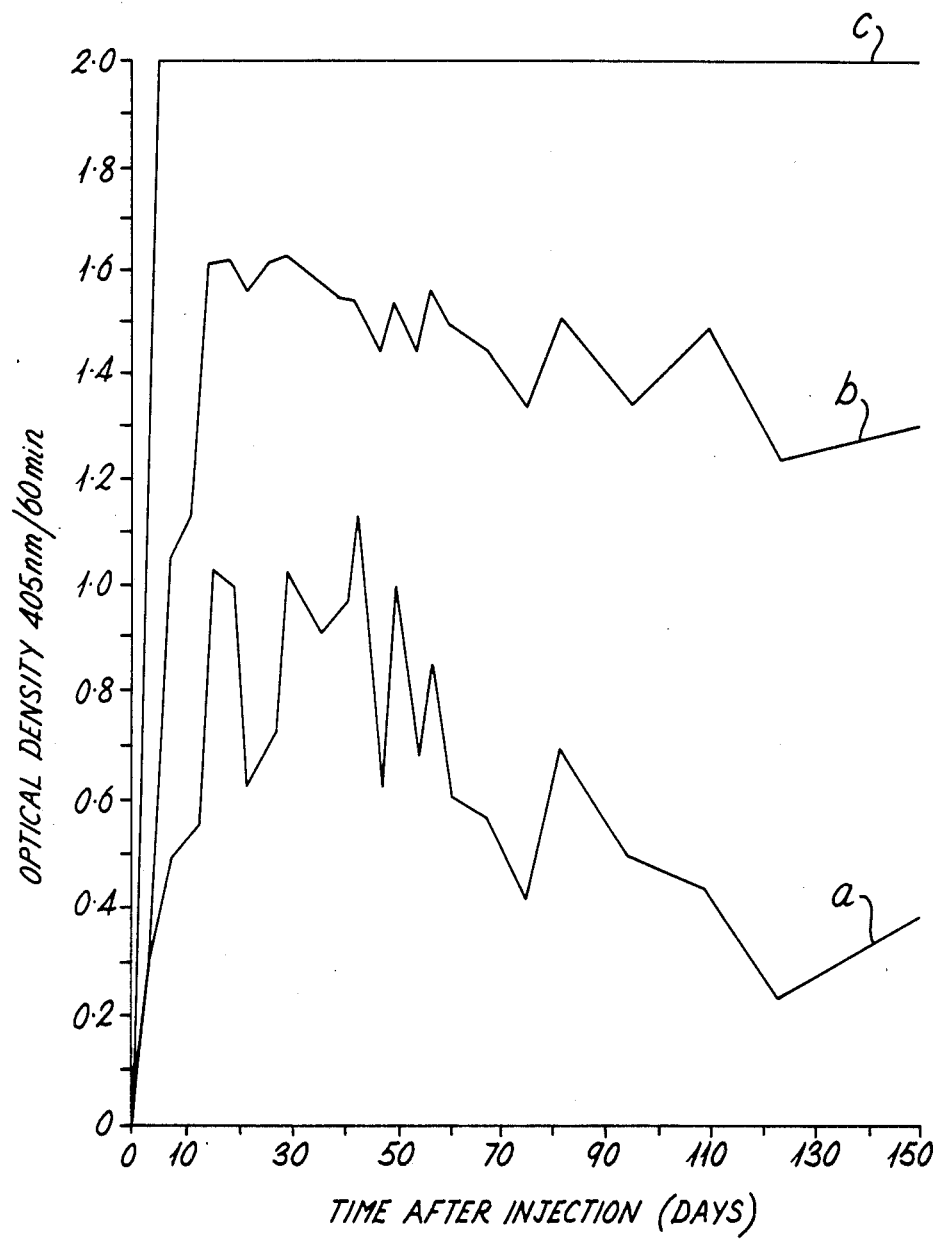
Figure 4:
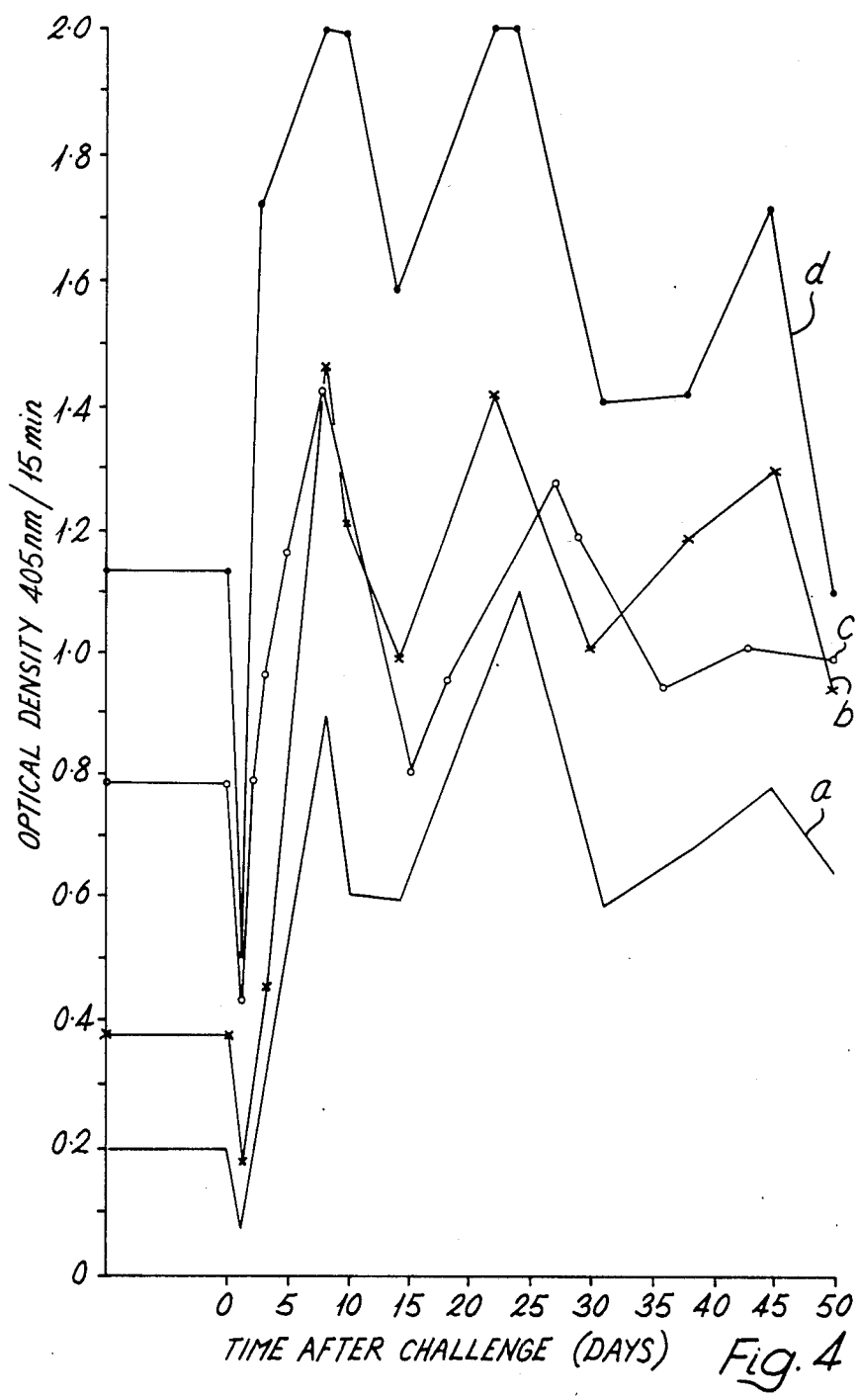

The resulting antibody levels in terms of the optical density readings in the ELSIA assay measured over a period of 160 days are shown in FIG. 3 where it will be seen that the osmicated microvesicle preparation exhibits significantly higher levels than even the 720 $\mu$g dose of an osmicated venom solution.

EXAMPLE 8

Enhancement of activity in mice of orally administered *Echis carinatus* venom through treatment with osmium tetroxide Groups of five mice were dosed orally using a blunt-ended wide bore needle with a single bolus of *E. carinatus* venom at day 0 in the form of three different preparations: (a) 200 $\mu$g dose of venom in doubly osmicated microvesicles prepared as described in Example 2; (b) 200 $\mu$g dose of venom as a 1% w/v solution in phosphate buffered saline to which has been added 10% v/v of 1% w/v aqueous osmium tetroxide; (c) 200 $\mu$g dose of venom as a simple 1% w/v solution in phosphate buffered saline.

The antibody levels resulting from the use of each form of preparation were assayed over varying periods of about 40-60 days using the ELISA assay procedure described in Example 3 with 60 minute readings. Neither preparation (b) nor preparation (c) gave an optical density reading at 405 nm which at any time rose above 0.1, this being the level above which a reading may be taken as being significant in terms of showing a positive antibody response to the administration of a preparation. In the case of preparation (a), however, the readings obtained were above 0.1 for day 13 to day 20 giving a clear indication of the production of a significant antibody titre in serum following oral administration of the doubly osmicated microvesicle preparation.

EXAMPLE 9

Enhancement of activity in mice of intravenously administered horseradish peroxidase through treatment with osmium tetroxide Mice are treated with different preparations of horseradish peroxidase at varying doses of the enzyme in the range of 3.75–15 mg/kg, groups of five mice being injected intravenously with the aliquot of each preparation, at the particular dosage rate, on a single occasion at day 0. The antibody levels resulting from the use of each form of treatment are assayed over an extended period of time by an ELISA assay using plates coated with 1 µg/ml of protein in a similar manner to that described for the assay procedure of Example 7.

The relative efficiency at generating antibodies was studied for three preparations consisting of: (a) 75, 150 or 300 µg dose of enzyme in singly osmicated mircovesicles prepared as described in Example 2; (b) 75, 150 or 300 ug dose of enzyme at a 1% w/v solution in phosphate buffered saline to which has been added 10% v/v of 1% w/v osmium tetroxide; (c) 75, 150 or 300 µg dose of enzyme as a simple 1% w/v solution in phosphate buffered saline.

The results obtained with these three types of preparation show, as in Example 7(A), higher antibody levels at any particular dosage level for the osmicated mocrovesicle preparation (a) as compared with the simple solution preparation (c). However, by contrast with the results reported in Example 7(C), the antibody levels achieved at any particular dosage level are higher for the osmicated solution preparation (b) than for the osmicated microvesicle preparation (a). Thus, the maximum antibody levels (in terms of optical density at 405 nm/60 minutes) recorded at 28 days after injection for both the 150 and 300 µg dosage levels are between 0.9 and 1.0 for preparation 8b) and between 0.7 and 0.8 for preparation (a).

EXAMPLE 10

Activity in mice of subcutaneously administered *Echis carinatus* venom in a double permanganated microvesicle preparation Mice were treated with a doubly permanganated microvesicle preparation of *E. carinatus* prepared as described in Example 6 using 500 µg to 2 mg dosages of the venom given subcutaneously. Each particular treatment was administered to a group of five mice on a single occasion at day 0 and the antibody levels resulting from each type of treatment were assayed over an extended period of time as described in Example 7. Significant antibody levels were achieved with each dose level of the venom, the maximum levels achieved corresponding in the case of dosages of 750 μg and above to the highest measurable reading of 2.0.

EXAMPLE 11

Efficacy of protection provided in mice by osmicated microvesicles incorporating *Echis carinatus*

Groups of five mice treated with doses of from 20–200 μg of *E. carinatus* venom formulated in singly osmicated microvesicles, as described in Example 7, were challenged after a period of 1 year with a subcutaneously administered lethal dose of 300 μg of the venom. The antibody levels in terms of the optical density readings in the ELISA assay described in Example 3 are followed for 50 days after challenge and are shown in FIG. 4 where plots (a), (b), (c) and (d) correspond to doses of 20 μg, 50 μg, 100 μg and 200 μg, respectively. The readings in this instance were 15 minute readings, 30 minute and higher readings rising to the highest measureable value of 2.0 very rapidly after challenge.

Despite the period of a year since the initial protective injection without the use of any booster injection, sixty per cent of the mice survived, these being among those with the higher initial antibody titres from the higher initial dose levels of venom.

EXAMPLE 12

Activity in sheep of various snake venoms administered intravenously as a doubly osmicated microvesicle preparation Sheep are treated either singly or in pairs by intravenous injection with doubly osmicated microvesicle preparations of various snake venoms prepared as described in Examples 3 and 4. An initial injection is given at day 0 followed in most cases by a booster injection of the same dose at about day 114 or 115. The antibody levels resulting from the use of each preparation are assayed over an extended period of time substantially as described in Example 6 for the experiments in mice, the serum dilution level being 1:50 except in the case of the *B. candidus* preparation where a 1:5 dilution level is employed in view of the slower build up of the antibody levels in this case.

This procedure was followed for the following preparations: 20 mg dose of *E. carinatus* venom, 10 mg dose of *B. candidus* venom, 10 mg dose of *T. albolabris* venom and 10 mg of *T. macrops* venom. The results obtained in two sheep with the *T. albolabris* venom are shown in FIG. 5 (where the change in the scale of the abscissa following the readings at 59 days should be noted) from which it will be seen that a high antibody level was produced after about 20 days which eventually declined, more rapidly in one sheep than the other, but was restored to its original level by the booster injection given at 114 days. The results obtained with the other three vaccines were basically similar except that with the elapid *B. candidus* venom the response was slower than with the other three, viper venoms.

We claim:

1. A method for use in the production of antibodies to a peptide or protein material which comprises administering to a non-human host a composition comprising a peptide or protei material and osmium or ruthenium tetroxide, and thereafter isolating from the host either cells sensitised to, or antibodies to, said peptide or protein material.

2. A method according to claim 1, in which the peptide or protein material comprises a pathogenic antigen, an enzyme or a peptide hormone, or an active fragment thereof.

3. A method according to claim 2, in which the peptide or protein material comprises an enzyme or a toxic component of snake venom, or an active fragment thereof.

4. Antibodies to a peptide or protein material whenever raised against that material by the use of a composition comprising said peptide or protein material together or ruthenium tetroxide.

5. Antibodies according to claim 4 raised against a composition which comprises osmium tetroxide as the oxide.

6. Antibodies according to claim 4 raised against a peptide or protein material which comprises a pathogenic antigen, an enzyme or a peptide hormone, or an active fragment thereof.

7. Antibodies according to claim 6 raised against an enzyme or a toxic component of a snake venom, or an active fragment thereof.

8. A composition for use in didgnosis which comprises antibodies according to claims 4.

9. A method for the production of antibodies to a peptide or protein material in a human or non-human patient which comprises administering to that patient either the said peptide or protein material together with osmium or ruthenium tetroxide, or antibodies raised in a non-human host by the administration to that host of a material which comprises said peptide or protein material together with such an oxide.

10. A method according to claim 9, in which the oxide is osmium tetroxide.

11. A method according to claim 9 in which the peptide or protein material comprises a pathogenic antigen, an enzyme or peptide hormone, or an active fragment thereof.

12. A method according to claim 11, in which the patient is treated with antibodies raised against a toxic component of a snake venom, or an active fragment thereof.

13. A method according to claim 1, wherein said composition comprises osmium tetroxide.

14. A method according to claim 1, wherein said composition is in microvesicle form.

15. A method according to claim 11, wherein the peptide or protein material comprises a toxic component of a snake venom or an active fragment of such a toxic component.

16. A method according to claim 9, wherein said peptide or protein material is administered i microvesicle form.

17. A method according to claim 9, wherein said antibodies are administered in microvesicle form.

* * * * *